United States Patent [19]

Puumalainen

[11] 4,147,931
[45] Apr. 3, 1979

[54] PROCEDURE FOR MEASURING UNIT AREA WEIGHTS

[76] Inventor: Pertti Puumalainen, Puistokatu 10 B 43, 70100 Kuopio 10, Finland

[21] Appl. No.: 845,969

[22] Filed: Oct. 27, 1977

[51] Int. Cl.² ............................................. G01N 23/20
[52] U.S. Cl. ..................................................... 250/273
[58] Field of Search ........................ 250/273, 272, 277

[56] References Cited

U.S. PATENT DOCUMENTS 2,977,478   3/1961   Wuppermann ...................... 250/272

Primary Examiner—Alfred E. Smith
Assistant Examiner—T. N. Grigsby

Attorney, Agent, or Firm—Toren, McGeady and Stanger

[57] ABSTRACT

A procedure for measuring unit area weights (base weights) in materials combinations comprising a base material, thereupon a precoating, and upon which latter there is a surface coating or coatings. The materials combination is irradiated with x-rays which excite the characteristic x-ray radiation of a substance in the precoat, the intensity of which is measured above and below the coated base material, in addition to which the absorption in the materials combination of the primary radiation from the radiation source is measured, whereby from the mutually independent results of measurement obtained the unit area weights of the different courses are calculated.

2 Claims, 1 Drawing Figure

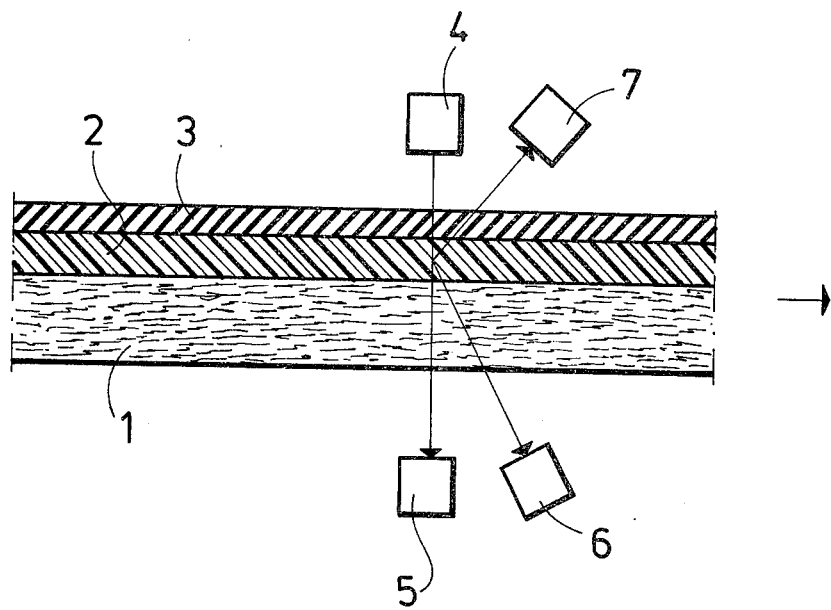

PROCEDURE FOR MEASURING UNIT AREA WEIGHTS

It is known in prior art to measure the unit area weight of a coating on paper by utilizing x-rays. The procedure is then: to add to the coating substance a given quantity of marker substance, in which capacity zinc oxide, for instance, has been used, and which is irradiated with primary x-rays. The x-ray radiation obtained from the specimen is composed of rays emitted when electrons return from higher to lower levels (fluorescence radiation) and of the rays originating in the scattering of the primary radiation, and which constitute the background radiation. The energy of the fluorescence radiation obtained is characteristic of the excited substance, and the intensity of the fluoresecence radiation at a given characteristic energy of the substance is proportional to the amount of substance present. It has been possible by the said method to measure coating weights with 2% accuracy within less than 6 seconds when 1 % zinc oxide was added to the coating colour.

The aim of the present invention is to provide a simple method for measuring, e.g. from a moving paper or cardboard web, the unit area weight of more than one layer, and in which connection no marker substance need be used in the coats, instead of which the measurement can be made directly from a specimen.

The procedure of the invention is characterized in that the materials combination is irradiated with x-rays which excite the characteristic x-ray radiation of a substance present in the precoat, and the intensity of which is then measured above and below the base material, in addition to which the absorption of the primary radiation from the radiation source in the materials combination is measured, whereby from the obtained, mutually independent results of measurement the unit area weights of the different courses are calculated. Above all, one achieves with the aid of the invention that the coating quantities can be continuously controlled to be exactly as desired, while in methods of prior art coating substances have been consumed in unnecessary excess. It is thus understood that a considerable amount of coating substances is saved by virtue of the present invention.

In the following, the procedure of the invention is described by the aid of an example, wherein the unit area weights of the coats upon a moving cardboard web are measured. The precoat of the cardboard was a $CaCO_3$ coat, and upon this there was caolin as surfacing coat. In the drawing, the cardboard has been indicated with reference numeral 1, the $CaCO_3$ coat thereupon with 2, and the topmost caolin coat with 3. The combination is irradiated with radiation from a $^{55}Fe$ radioisotope source 4, the x-rays emitted by this source exciting the characteristic secondary x-ray radiation of the calcium present in layer 2, and the intensity of which is measured by means of detectors 6 and 7 on both sides of the cardboard 1. The detector 5 is furthermore used to measure the absorption of the primary radiation from the $^{55}Fe$ source in the cardboard-coating combination. From the results of measurement obtained, which are mathematically dependent on the unit area weights of each coat, the unit area weights of both coating layers ($CaCO_3$ and caolin) and of the cardboard are found by the principle of solving three equations for three unknown. If the detectors 5, 6 and 7 are directly connected to a computer, the procedure may be applied on-line in a paper or cardboard coating machine. It is then possible to achieve a measuring accuracy of $\pm 0.5$ $g/m^2$ with a measuring interval of 10–20 sec. The invention is not confined to the example presented, and it may be varied within the scope of the claims.

I claim:

1. Improvement in a procedure for measuring unit area weights in material combinations having a base material, thereupon a precoat and upon which latter there is a surfacing coat or coats, wherein the improvement comprises that the materials combination is irradiated with x-rays which excite the characteristic x-ray radiation of a substance in the precoat, the intensity of which is measured above and below the coated base material, in addition to which the absorption in the materials combination of the primary radiation from the radiation source is measure whereby from the mutually independent results of measurement obtained the unit area weights of the different courses are calculated.

2. Procedure according to claim 1, characterized in that the materials combination is cardboard or paper overlayed with a $CaCO_3$ precoat and upon this latter as surface coating, caolin.

UNITED STATES PATENT OFFICE
CERTIFICATE OF CORRECTION

Patent No. 4,147,931   Dated April 3, 1979

Inventor(s) Pertti Puumalainen

It is certified that error appears in the above-identified patent and that said Letters Patent are hereby corrected as shown below:

In the heading of the Patent [30] should read as follows:

[30]  Foreign Application Priority data:

Dec. 18, 1976   Finland............763572

Signed and Sealed this

Eleventh Day of September 1979

[SEAL]

Attest:

LUTRELLE F. PARKER
*Attesting Officer*   *Acting Commissioner of Patents and Trademarks*